United States Patent [19]

Mayer et al.

[11] Patent Number: 5,312,935
[45] Date of Patent: May 17, 1994

[54] PURIFICATION OF FLUORINATED CARBOXYLIC ACIDS

[75] Inventors: Ludwig Mayer, Burghausen; Gernot Löhr, Burgkirchen, both of Fed. Rep. of Germany

[73] Assignee: Hoechst Aktiengesellschaft, Frankfurt am Main, Fed. Rep. of Germany

[21] Appl. No.: 50,874

[22] Filed: Apr. 21, 1993

[30] Foreign Application Priority Data

Apr. 22, 1992 [DE] Fed. Rep. of Germany ....... 4213154

[51] Int. Cl.$^5$ .......................... C02F 1/72; C07C 53/21
[52] U.S. Cl. .................................. 554/182; 554/181; 554/183; 562/605; 210/758; 210/759; 203/15
[58] Field of Search ................ 562/605; 554/181, 182, 554/183; 203/15; 210/758, 759

[56] References Cited

U.S. PATENT DOCUMENTS

| | | |
|---|---|---|
| 3,709,795 | 1/1973 | Singleton . |
| 3,833,626 | 9/1974 | Ferse et al. . |
| 4,609,497 | 9/1986 | Cope ................................... 562/605 |
| 4,751,027 | 6/1988 | von Werner et al. .............. 562/605 |

*Primary Examiner*—Neil M. McCarthy

[57] ABSTRACT

Fluorinated carboxylic acids which do not have the required purity for use as emulsifier in the polymerization of fluorinated monomers can, if necessary after prior de-watering, be treated with oxidants, whereupon the isolation of the pure product is carried out by crystallisation or, preferably, by distillation.

17 Claims, No Drawings

PURIFICATION OF FLUORINATED CARBOXYLIC ACIDS

For the polymerization of fluorinated monomers in aqueous dispersion, fluorinated emulsifiers are used, since these show no telogenic activity. Highly soluble salts of perfluorocarboxylic acids are principally used, in particular the ammonium salt of perfluorooctanoic acid. For this purpose, the base acids must have a high purity since impurities can inhibit or even prevent the initiation of polymerization, interferences in the course of polymerization can occur, for example by chain transfer, or a termination of the polymerization can occur.

Such interferences are frequently observed even with the use of commercial products, even if no impurities are observable in them. It is therefore recommended for use as emulsifiers to subject the base fluorinated acids to a special purification.

It is known from the published Japanese Patent Application 89/117840 to obtain n-perfluorooctanoic acid in pure form from a mixture with isoperfluorooctanoic acid by crystallization with aqueous chloroform. However, chloroform is toxic and is considered to be carcinogenic, so that an industrial realization of this process would be accompanied by exceptional expenditure.

It has now been found that fluorinated carboxylic acids can be converted to the required purity mentioned if the starting material is initially, if required, substantially de-watered, the low-water product is treated with oxidants and the pure product is isolated.

The low water content required for the treatment with the oxidant can depend on the type and the amount of the impurities and the choice of the oxidant and is expediently determined by simple preliminary tests. Water amounts of less than 2% by weight do not generally interfere.

Products can serve as the starting material which have been obtained from 1-iodoperfluoroalkanes, for example by the process of U.S. Pat. No. 4,400,325. Furthermore, products which have been obtained from effluents with the aid of basic anion exchangers are suitable, for example products according to the process of U.S. Pat. No. 4 282 162. If the process is used for commercial "pure materials," depending on their water content, the de-watering step can be dispensed with.

The de-watering of the starting material can be carried out in a manner known per se, that is by the addition of dehydrating agents or by physical methods. The dehydrating agents used are principally salts such as sodium sulfate or calcium chloride, although their use can impair further processing, that is the oxidation or the isolation of the pure product. Drying agents such as phosphorus pentoxide, but especially concentrated sulfuric acid, sulfur trioxide or mixtures thereof ("oleum") are therefore advantageously selected.

Among the physical de-watering methods, distillation is preferred, especially if the isolation of the pure product is also to be carried out by distillation. In this embodiment of the invention, in a first step the interfering water content is thus reduced and, expediently in the same apparatus, after the treatment with the oxidant, the pure product is distilled off.

Although the fluorinated carboxylic acids to be purified are relatively strong acids, the addition of still stronger acids is recommended, such as for example concentrated sulfuric acid, since the oxidants show their best activity in the acid range.

The treatment with the oxidant is expediently carried out with heating to a temperature at which thorough mixing is ensured. The procedure is advantageously carried out in a homogeneous liquid phase, for example in the range from about 60° C. to the boiling point of the mixture.

The type and amount of the oxidant are expediently chosen on the basis of simple preliminary trials, in particular when, as is common, the type and extent of the impurities are not known or are not known precisely enough. A polymerization batch of tetrafluoroethylene (TFE) with ammonium persulfate as initiator under standard conditions can serve as a criterion of success.

All redox systems having standard electrode potentials greater than $+1.30$ V, preferably dichromates and permanganates and especially persulfates such as sodium persulfate, potassium persulfate or ammonium persulfate serve as oxidants.

The isolation of the purified fluoroalkanoic acid can be carried out by crystallisation. n-Perfluorooctanoic acid melts at 54° to 55° C. Crystallisation can thus be carried out in this case by appropriate, expediently slow, cooling, with or without addition of a solvent such as water which keeps the undesired constituents of the reaction mixture in solution.

The isolation of the purified product by distillation is advantageous, if desired under reduced pressure. n-Perfluorooctanoic acid boils at 113° C. at a pressure of 5.3 kPa. Isolation at the high purity desired is therefore possible by fractional distillation in the vacuum of a water-jet pump.

The fluorocarboxylic acids purified according to the invention, in the form of their readily soluble salts, preferably the ammonium salts, are suitable as emulsifiers for the polymerization of fluorinated monomers in aqueous dispersion. The invention thus permits the recovery of these valuable substances in high yields even from contaminated and highly dilute media, for example from production effluents.

Preferred embodiments of the invention are apparent from the following examples. Percentage FIGURES are based on the weight.

EXAMPLE 1

3,000 g of a salt paste having the following composition:
approximately 40% sodium salt of perfluorooctanoic acid (PFOA)
approximately 20% sodium sulfate
below 5% sodium hydroxide
approximately 40% water
are placed in a 6 l stirred flask furnished with a bottom drainage cock and heating mantle.

300 ml of concentrated sulfuric acid are added dropwise in about 20 minutes with slow stirring of the salt paste at 20° C.

The flask contents at approximately 50° to 60° C. are heated to 65° C., placed into a separating funnel and the PFOA bottom phase (1,303 g, water content: 9%) is isolated. In a 500 ml stirred flask, 80 g of oleum ($SO_3$ content: 20%) are added to 200 g of this water-containing crude PFOA, the mixture is heated to about 60° C. and 14 g of ammonium peroxodisulfate (APS) are added in small portions with stirring. Intense heating and vigorous foaming occur during this. This mixture is kept at 100° to 110° C. for 7 hours with slow stirring.

After attachment of a short column section and a column head heated to 60° C., after removal of about 10% of first runnings, the PFOA is distilled over in the vacuum of a water-jet pump (amount of the main run: 115 g). The PFOA is colorless and does not change even over several months. In the TFE polymerization or TFE copolymerization, in comparison to highly pure commercial product no differences can be determined with respect to TFE uptake, molecular weight of the resulting polymer, initiator consumption or similar.

EXAMPLE 2

80 g of concentrated sulfuric acid are added to 200 g of a brown-discolored, dry PFOA, obtained by the process of U.S. Pat. No. 4,282,162, in a 500 ml stirred flask, the mixture is heated to about 60° C. and 14 g of APS are added in small portions. This mixture is kept at 100° to 110° C. for 7 hours with slow stirring. After attaching a short column section and a column head heated to 60° C., after removal of about 10% first runnings, the PFOA is distilled over in the vacuum of a water-jet pump (amount of the main run: 159 g). The PFOA is colorless and does not change further.

. This APS-treated resulting PFOA is of "polymerization grade," that is TFE polymerization and copolymerization can be carried out within the conventional statistically monitored process parameters.

EXAMPLE 3

40 g of concentrated sulfuric acid are added to 102 g of a sodium perfluorooctanate-containing salt mixture of the following composition:
about 53% sodium salt of PFOA
about 36% sodium sulfate
about 6.5% sodium hydroxide
4.5%-water
in a 500 ml stirred flask and the mixture is heated to about 60° C. 7 g of sodium dichromate are added with stirring. This mixture is kept at 100 to 120 C. for 5.5 hours with slow stirring.

After attaching a short column section and a column head heated to 60° C., the PFOA is distilled over in the vacuum of a water-jet pump. 41 g of colorless PFOA are obtained, which do not change further.

COMPARISON EXAMPLE 40 g of concentrated sulfuric acid are added to 200 g of brown-discolored crude PFOA, having 9% water content, in a 500 ml flask and the mixture is distilled via a short column section and a column head heated to 60° C. in the vacuum of a water-jet pump. After removing about 10% of first runnings, 142 g of PFOA is distilled off as the main run. The PFOA is colorless, but discolors in about 7 days to dark brown.

If TFE polymerization tests are carried out using this PFOA, in comparison to the PFOA from Example 1 or Example 2, increased run times and the formation of lower molecular weights are observed.

We claim:

1. A process for the purification of an impure perfluorinated carboxylic acid, which process comprises: oxidizing the impurities in a reaction mixture comprising a water content of less than about 9% by weight, impure perfluorinated carboxylic acid and an oxidant, thereby purifying said acid, and isolating the resulting purifies perfluorinated carboxylic acid.

2. The process as claimed in claim 1, wherein said water content is less than 2% by weight.

3. The process as claimed in claim 1, wherein said perfluorinated carboxylic acid has been obtained from a starting material having a water content having been reduced by physically removing water from said starting material or treating said starting material with a chemical dehydrating agent.

4. The process as claimed in claim 3, wherein the water content has been reduced by adding to said starting material a chemical dehydrating agent, said chemical dehydrating agent being sulfur trioxide, concentrated sulfuric acid, or a combination thereof.

5. The process as claimed in claim 3, wherein the water content has been reduced by distilling water from said starting material.

6. The process as claimed in claim 1, wherein said oxidizing step is carried out by heating said reaction mixture to a temperature which ensures thorough mixing of the reaction mixture.

7. The process as claimed in claim 6, wherein said oxidizing step is carried out by heating the reaction mixture to a temperature from 60° C. to the boiling point of the reaction mixture.

8. The process as claimed in claim 1, wherein said oxidant is a redox system having a standard electrode potential greater than +1.30 V.

9. The process as claimed in claim 8, wherein said oxidant is a persulfate, a permanganate, or a dichromate.

10. The process as claimed in claim 1, wherein said isolating step is carried out by distilling the resulting purified perfluorinated carboxylic acid.

11. The process as claimed in claim 1, wherein said starting material comprises an impure fluorinated carboxylic acid or fluorinated carboxylic acid salt containing a polymerization-inhibiting or chain-transferring or chain-terminating impurity.

12. The process as claimed in claim 1, wherein said reaction mixture contains an acid which is a stronger acid than the perfluorinated carboxylic acid in order to enhance the effectiveness of the oxidant.

13. The process as claimed in claim 3 wherein said starting material comprises an impure salt of a perfluorinated carboxylic acid and said salt is converted to the corresponding acid and also de-watered by contacting it with concentrated sulfuric acid.

14. The process as claimed in claim 13, wherein the resulting corresponding acid has a water content of less than 2% by weight.

15. The process as claimed in claim 13, wherein said oxidant is a persulfate, a permanganate, or a dichromate.

16. The process as claimed in claim 13, wherein said starting material comprises an impure salt of perfluorooctanoic acid.

17. A process as claimed in claim 1, wherein the perfluorinated carboxylic acid in said reaction mixture is perfluorooctanoic acid.

* * * * *